March 26, 1957 H. BOS Plant Pat. 1,584
ROSE PLANT
Filed Oct. 27, 1955
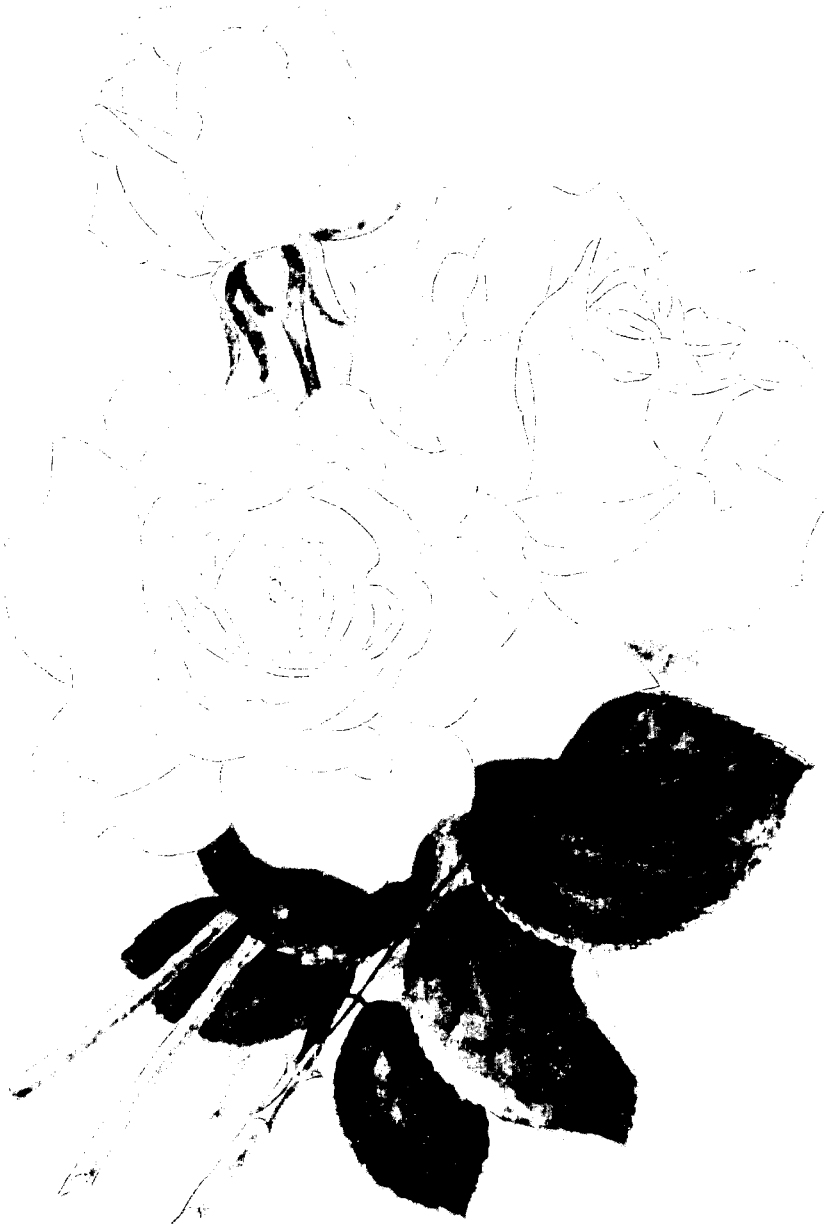
WITNESS
Addison T. Avery
INVENTOR
HENRY BOS
Kummler, Kummler & Snow
ATTYS.

United States Patent Office

Plant Pat. 1,584
Patented Mar. 26, 1957

1,584

ROSE PLANT

Henry Bos, Melrose Park, Ill., assignor to The Premier Rose Gardens, Consolidated, Des Plaines, Ill., a corporation of Illinois Application October 27, 1955, Serial No. 543,290

1 Claim. (Cl. 47—61)

The new and distinct variety of rose plant, herein described and illustrated, is a sport, discovered by me at nursery gardens located at Des Plaines, Illinois, of the well-known rose "Pink Delight," unpatented, which parent variety was imported from Kordes, Germany, and originated as a cross between "Senator" and "Florex," both also unpatented. My new variety has been asexually reproduced in Illinois and California, by budding, grafting and rooting since November 1953, and its characteristics appear to be permanently fixed. At the present time more than 10,000 plants have been budded in California and in Maywood, Illinois, and many have been propagated by rooting the plants in sand.

The primary object in propagating this new variety was to retain certain noted improvements over the normal characteristics of the parent variety, and over those of another sport of the same parent variety disclosed in Plant Patent No. 740; the particular improved characteristics being a larger flower, a greater number of petals, a deeper and longer lasting shade of pink, and a bloom with much more fragrance.

In addition to possessing the foregoing improved characteristics, my new variety of rose opens more slowly than the parent plant, and always maintains a solid center. This new plant grows vigorously, blooms more freely and profusely, blooms continuously the year around, and the cut flower has longer lasting qualities. It is a thriving, healthy plant through the summer months and the petals of the flowers hang on for a considerably longer time than the parent variety.

The accompanying illustration shows, in full color, specimens of this new variety in various stages of development.

Like the before-mentioned sport, Plant Patent 740, the flower is a large double blossom of uniform pink coloring, shading from a deep pink in the compact central grouping of petals to the light pink of the outer petals; but the pink is a deeper shade and more intense than that of the said sport. Its petals also have a suede-like satiny sheen, and there is a sufficient quantity of large, dark green foliage in the full plant to give a pleasing green background to the pink of the blooms. Also the bud is urn-shaped, but its sepals are of a darker shade than either the parent plant or the said sport.

Unlike the parent plant and its said sport, Plant Patent 740, the bud of the new variety is larger, averaging an inch in diameter at the base and a length of 1½ inches. The flower is also larger being 3 inches to 4 inches in diameter when fully open; about 3 inches in diameter when half open; and averaging a depth of 2 inches. The flower also has 30 or more petals, with a tightly packed middle area and a full high center; and the corolla is borne on sturdy upright stems. Another distinguishing feature is that, while both the parent plant and the variety of Plant Patent 740 have rather delicate rose scent, the fragrance of my new variety is very much stronger and permeates an entire room in which the blooms are placed.

The following is a detailed description of my new variety:

Flower: Blooms continuously the year around and more profusely than the parent plant.

- Size.—3½ to 4 inches in diameter when fully open; 2 inches in depth both when half open and fully open.
- *Borne.*—Singly.
- *Shape.*—When first opens is cup-shape with a high center.
- *Petalage.*—30 or more.
- *Texture.*—Like suede.
- *Appearance.*—Satiny.
- *Affected by wet or hot weather.*—No. Does very well through the hot summer months.
- *Persistence.*—Petals hang on.
- *Discoloration.*—None.
- *Fragrance.*—Intense and penetrating.
- *Lasting quality.*—Very good both on plant and as a cut flower.

Bud:

- *Size.*—1 inch at base. 1½ inches in length.
- *Form.*—Urn-shaped.
- *Color.*—Dark pink when sepals first divide, becoming a lighter tint when petals begin to unfurl.

Sepals: "Hooded" over bud. Curl back and are covered by petals. Do not fall off.

Plant:

- *Form.*—Bush.
- *Height.*—5 to 6 feet at 4 years.
- *Growth.*—Vigorous.
- *Branching.*—Yes.
- *Stems.*—36 to 48 inches in length.

Foliage:

- *Quantity.*—Average amount.
- *Size of leaf.*—Large.
- *Texture.*—Glossy and smooth.

Thorns: 1 or 2 toward base of stem.

Color designations according to "A Dictionary of Color by Maerz and Paul" are as follows:

| Part | Plate | Letter | No. |
|---|---|---|---|
| Palest shade at edge of bloom | 49 | D to E | 1 |
| Shading into | 49 | J | 3 |
| Deepest shade of bloom | 1 | E to H | 5 |
| Top of leaf | 24 | L | 9 |
| Underside of leaf | 21 | J | 6 |
| Stem | 21 | L | 7 |

The larger size of the flower, greater number of petals, compact high centers, deeper pink coloring, and greatly increased fragrance, combined with the advantages that the bloom opens more slowly, always maintains a high solid center, is carried on sturdy stems, and has very good keeping qualities and strong resistance to summer heat, has provided a greatly improved and commercially popular new variety of rose plant.

Having thus disclosed my invention, I claim:

A new and distinct variety of rose plant, substantially as shown and described, characterized particularly by its vigorous constitution; its continuous and free blooming habit; the depth, brilliance and uniformity of the pink color of the flowers; the larger flower with increased number of petals, which open more slowly and always maintain a solid center; the sturdy long stems; the deep and lasting fragrance of the flowers; and the good keeping qualities of the flowers both on the plant and when cut.

No references cited.